United States Patent [19]

Maurer et al.

[11] Patent Number: 5,182,588
[45] Date of Patent: Jan. 26, 1993

[54] LENS FOR FILTERING VISIBLE AND ULTRAVIOLET ELECTROMAGNETIC WAVES DURING DENTAL PROCEDURES

[76] Inventors: Robert D. Maurer, 2700 W. Dimond Blvd., Anchorage, Ak. 99502; Timothy B. McLaughlin, c/o Anchorage Eye Association, 800 E. Dimond, Ste. 228A, Anchorage, Ak. 99515

[21] Appl. No.: 724,149

[22] Filed: Jul. 1, 1991

[51] Int. Cl.$^5$ ............................ G02C 7/10; A61C 5/00
[52] U.S. Cl. .................................. 351/165; 433/226
[58] Field of Search ................. 351/163, 164, 165; 433/226

[56] References Cited

U.S. PATENT DOCUMENTS

| | | | |
|---|---|---|---|
| 1,257,667 | 2/1918 | Barr | 351/163 |
| 1,865,715 | 7/1932 | Tillyer | 351/164 |
| 2,334,446 | 11/1943 | Serrell | 351/163 |
| 2,964,427 | 12/1960 | Rheinberger et al. | 117/33.3 |
| 3,588,216 | 6/1971 | Bloom | 350/1 |
| 3,628,854 | 12/1971 | Jampolsky | 351/165 X |
| 3,826,564 | 7/1974 | Werling, Sr. | 351/165 X |
| 4,320,939 | 3/1982 | Mueller | 351/44 |
| 4,758,079 | 7/1988 | Bledsoe | 351/44 |

OTHER PUBLICATIONS

Clinical Research Associates, vol. 8, Issue 2, Feb. 1984.
Clinical Research Associates, vol. 9, Issue 1, Jan. 1985.

*Primary Examiner*—Scott J. Sugarman
*Attorney, Agent, or Firm*—Christensen, O'Connor, Johnson & Kindness

[57] ABSTRACT

Lenses coated with a UV light absorbing coating and a blue light absorbing coating protect the eyes of a dental practitioner from harmful radiation emitted by a light source used during dental curing procedures. The lenses include a clear portion which allows the wearer to view the treated area without a loss of contrast encountered when the treated area is viewed through the portion of the lenses provided with the blue light absorbing coating.

9 Claims, 2 Drawing Sheets

LENS FOR FILTERING VISIBLE AND ULTRAVIOLET ELECTROMAGNETIC WAVES DURING DENTAL PROCEDURES

FIELD OF THE INVENTION

The present invention relates to a lens for filtering visible and ultraviolet electromagnetic waves emitted by a high intensity light source used in dental procedures.

BACKGROUND OF THE INVENTION

Currently, composite restorative filling materials are used extensively by dentists. These materials are synthetic polymers and are typically used in bonding techniques. The composite material is generally applied as a viscous material which is hardened by polymerization. The polymerization of the viscous composite material is also known as a curing step. Many of the present day composite materials are cured by exposing the material with a high intensity light source that includes wavelengths in the ultraviolet and visible regions of the electromagnetic spectrum. It is presently estimated that about 60 percent of dental restorations use light curing techniques. Forecasts predict that in the future as many as 95 percent of dental restorations will use light curing.

Medical studies indicate that exposing the eye to ultraviolet light and blue light in the visible spectrum cause discomfort, reduced vision, and may accelerate or worsen ocular disorders. Specifically, exposure to ultraviolet light has been linked to cornea, lens, and retinal damage, and is believed to be a major cause of yellow-brown cataracts. Exposure to blue light in the visible spectrum has been linked to retinal damage, ocular degeneration, retinitis pigmentosa, night blindness, haze and glare.

At present, the available choices for protecting the eyes of a dental team from an intense light source involves significant compromises. For instance, conventional safety glasses having their entire lenses treated to provide protective filtering of the ultraviolet and blue light are available. Though effectively protecting the eye, this type of eye protection requires the dental team to view the entire field of treatment through the protective layer. The view is entirely shaded which gives a distorted color to teeth, tissue, emitted blood, etc. The distorted colors lead to a lack of contrast among the various elements in the mouth which makes it difficult for the dental team to observe and evaluate the procedure. While the safety glasses can be removed from the wearer's eye to observe the treated area after the light source is disconnected from the power source, the fact that the dental team normally has its hands full makes removal of the glasses cumbersome.

Another choice of eye protection is a colored, handheld panel that is usually held by a dental assistant. This shield is positioned between the area being exposed to the intense light and the line of vision of the dental team. This protective measure suffers from the same problem associated with the totally colored lenses of the eyeglasses described above, i.e., a lack of contrast in the viewing field. Furthermore, the assistant holding the shield is unable to perform other manual procedures normally needed. As a result, the shield is often not held in place, which results in no protection to the dental team.

Certain devices that serve as sources for the intense light also include a small protective shield mounted on the end of the light source. This shield is generally rotatable so that the shield can be placed within the line of view of the dental team, while the ultraviolet and blue light is being emitted. In addition to the contrast problems described above, the shield's close proximity to the end of the light source, which is normally placed close to or in the mouth, prevents the entire device from being utilized in tight quarters. Generally, if the shield is reduced in size significantly to improve access, the majority of protection is lost.

Existing types of eye protection provide a certain level of eye protection, as discussed above; however, each suffer from significant drawbacks. These drawbacks have left the dental team with the choice of either viewing the treated area with a undesirable loss of contrast, or not using eye protection at all. Accordingly, for at least 10 years, there has been a need in the dental industry for a type of eye protection that will protect the wearer from the ultraviolet light and blue light generated by the light sources used to cure composite materials. The device must be convenient to use and not suffer from the drawbacks of the existing types of eye protection.

SUMMARY OF THE INVENTION

The present invention is a lens that protects the eyes from the harmful effects of ultraviolet light and visible light in the blue spectrum generated by light sources used by dental teams to cure composite materials, such as restorative filling materials. The lens allows the wearer to selectively choose when protection from the harmful ultraviolet and blue light in the visible spectrum is needed, while keeping his or her hands free to complete other necessary tasks. The lens absorbs ultraviolet and blue light to protect the eyes. The lens is made from a strong material which allows the lens to serve the additional purpose of shielding the eyes from propelled debris, bacteria and other airborne emulsions, blood, and other emittents from the patient's mouth and surrounding work area.

The lens includes an ophthalmic lens that absorbs ultraviolet electromagnetic waves. The opthalmic lens has a first lens surface having a blocking portion that absorbs harmful electromagnetic waves in the visible spectrum. The blocking portion occupies less than a lower half of the first lens surface. Absorption of electromagnetic waves in the visible spectrum is achieved by coating a portion of the lower half of the opthalmic lens with a material that absorbs eletromagnetic waves. Since less than a lower half of the first lens surface is coated, the balance of the opthalmic lens is clear, which allows the wearer to selectively observe the treated area though the clear portion or coated portion depending on the degree of eye protection needed. The wearer can look through either the clear or coated portion of the lens by simply tilting his or her head. Viewing the work area through the clear portion avoids the contrast problems discussed above without requiring that the lens be removed from the wearer's head. Viewing the working area through the coated portion protects the wearer's eye from harmful ultraviolet and visible light emitted by the light source.

BRIEF DESCRIPTION OF THE DRAWINGS

The present invention will become more apparent from the following description when considered together with the accompanying drawings. Such drawings are set forth as being merely illustrative of the invention and are not intended in any way to be limitative thereof. It is to be understood that modifications and changes in the preferred embodiments of the invention herein described and shown will be made without departing from the spirit and scope of the present invention.

DETAILED DESCRIPTION OF THE INVENTION

Figure 1:
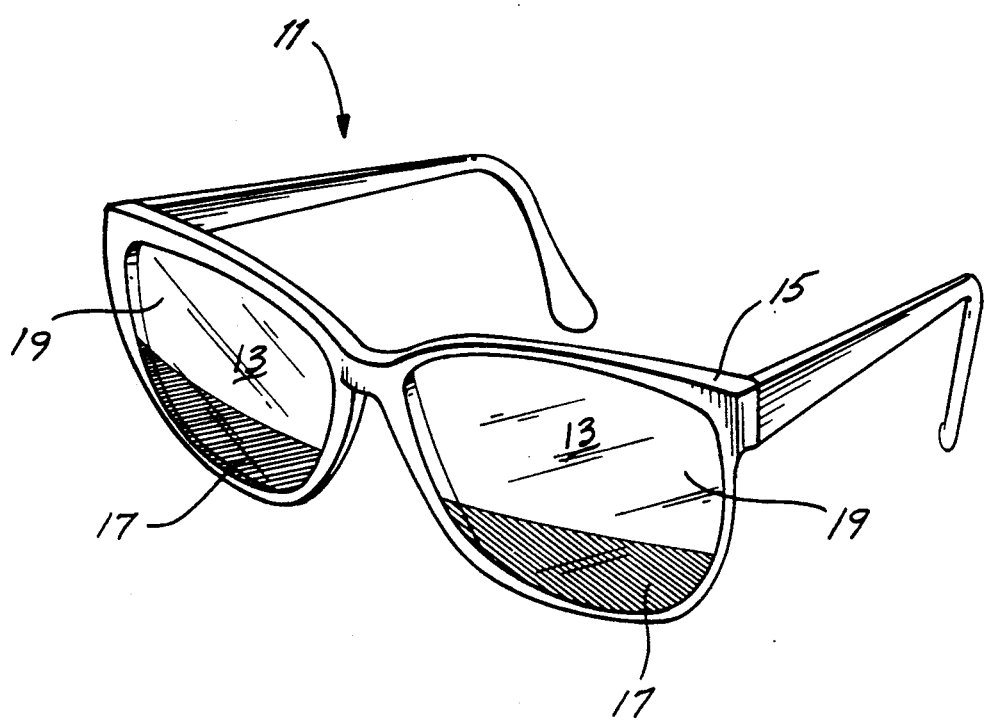
FIG. 1 is a perspective view of a pair of eyeglasses, including a lens formed in accordance with the present invention.
Figure 2:
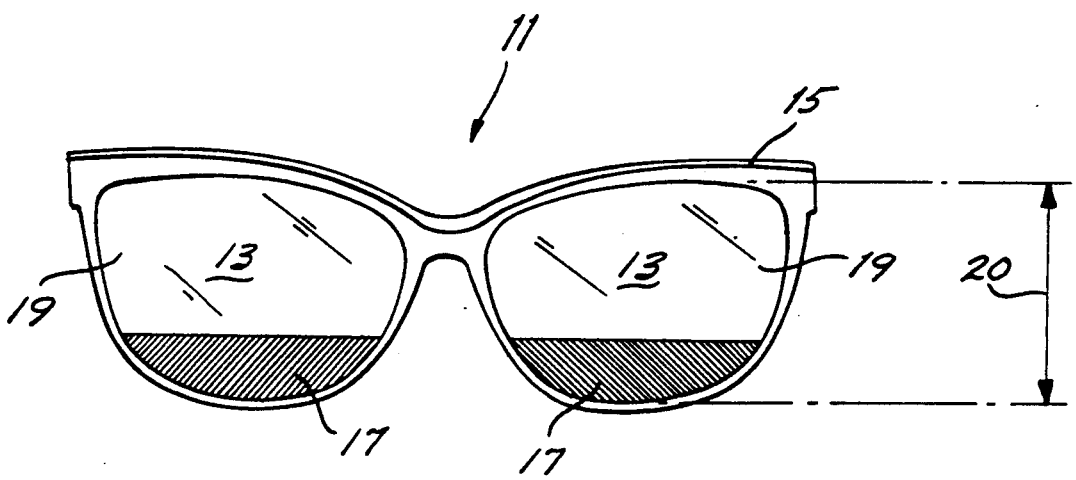
FIG. 2 is an elevation view of the front of the eyeglasses in FIG. 1.

Referring to FIGS. 1 and 2, a pair of glasses represented by reference numeral 11 includes lenses 13 formed in accordance with the present invention and a conventional eyeglasses frame 15 for holding lenses 13. Lenses 13 include a coated portion 17 and a clear portion 19. Lenses 13 include a vertical dimension indicated by reference numeral 20. Coated portion 17 is located on the lower half of lenses 13. Clear portion 19 is positioned above coated portion 17 and makes up the balance of lenses 13.

Lenses 13 are made from materials generally approved for use as ophthalmic lenses. The material chosen for lenses 13 should be optically clear and protect the eye from propelled debris, bacterial and other airborne emulsions, blood, and other emittents from the oral cavity and surrounding working area. Generally, those materials thought to be satisfactory for traditional safety glasses are appropriate. Such materials include approved plastics such as a plastic designated as CR-13. Polycarbonate can also be used in a lens formed in accordance with the present invention. Lens 13 can also be formed from glass; however, glass lenses are not as safe as plastic and polycarbonate lenses because of their greater susceptibility to breakage. Furthermore, glass lenses tend to be more difficult to provide with the protective coatings described below.

Prefearably, all portions of lenses 13 absorb ultraviolet electromagnetic waves emitted by light sources used by dentists to cure composite restorative filling materials. Ultraviolet electromagnetic waves generally refers to electromagnetic waves having wavelengths ranging from about 4 to 400 nanometers. Hereinafter ultraviolet electromagnetic waves will be referred to as UV light. One way of providing lenses 13 with the ability to absorb UV light is to apply a protective coating to lenses 13. Such types of UV light absorbing coatings are conventional and readily available from commercial sources such as Western Optical Supply of Hollywood, Ca. Although the compositions of many commercially available UV light absorbing coatings are proprietary, suitable coatings can be generally produced by conventional techniques using benzophenones, benzotriazoles, substituted acrylonitriles, and/or phenol-nickel complexes. A commercially available coating should be applied per the manufacturer's recommended procedure. Generally, for the UV light absorbing coating from Western Optical Supply, this procedure involves dipping the entire lens in a heated bath of the liquid coating. Satisfactory coatings have been achieved with dipping times on the order of 30 minutes. If a coating is used to enable a lens to absorb UV light, it is preferred that a plastic lens be chosen. Plastic lenses are preferred because applicants have found that plastic lenses are more receptive of the UV light absorbing coating material compared to glass lenses.

Lenses 13 include an inner lens surface and an outer surface opposite the inner surface. The inner refractive surface would be closer to the eye than the outer surface when the lenses are positioned in a frame on a wearer's head. The UV light absorbing coating can be applied to either the inner or outer surface. The portion of the inner or outer lens surface that is coated with the UV light absorbing material can vary so long as it is substantially co-extensive with the portion that is coated with the material that absorbs light in the blue region of the visible spectrum as described below. Preferably, the entire inner and/or outer surface is coated with the UV light absorbing coating in order to provide protection from UV light no matter what portion of the lens is viewed through by the wearer.

In order for lenses 13 to include portions 17 that absorbs potentially eye-damaging visible light, preferably, visible light having a wavelength less than about 530 nanometers, conventional coatings can be used. Such conventional coatings should absorb electromagnetic waves having a wavelength of about 530 nanometers or less, and preferably wavelengths that fall substantially within the blue region of the visible spectrum, e.g. 450-500 nanometers. Examples of such types of blue light absorbing coatings are sold under the name True Tint and Blue Light Blocker by Practical Systems, Inc., of Tarpin Springs, Fla. Blue Light Blocker is particularly convenient because it also absorbs UV light, and accordingly a UV and blue light absorbing coating can be provided by applying a single coating material. As with the UV light-absorbing coatings, commercially available compositions that absorb blue light are generally proprietary. The blue light absorbing coatings should be applied according to the manufacturer's specifications. Generally, the blue light absorbing coating is applied by dipping the lenses coated with the UV light absorbing coating in a heated bath of the blue light absorbing coating. When Blue Light Blocker is used, the lenses need not be precoated with a UV light absorbing coating, since the Blue Light Blocker will provide UV light absorption for the coated portions of the lenses. Satisfactory coating of plastic lenses are achieved with dipping times on the order of six hours. In order to coat only the lower portion of the lens, the upper portions are covered with a material impermeable to the blue light absorbing coating. First aid paper tape covered with duct tape provides satisfactory results.

The coating that absorbs blue light is applied to less than the lower half of lenses 13. Preferably, the blue light absorbing coating is applied to less than the lower one-third of lenses 13 in order to block the blue light while also providing a field of view through the clear portion of lenses 13 that is larger than the treated area, e.g., the patient's mouth. For ease of manufacturing, no boundary is established for the horizontal dimension of the coated portion of lenses 13, other than the sides of lenses. However, the coated portion need not necessarily extend to the edges of the lenses provided effective blocking of blue light is provided. Applicants consider the blocking of blue light effective when the elements of the eye susceptible to damage by blue light, e.g., the retina, are protected from the blue light. It must be appreciated that the amount of lenses 13 that are coated with the blue light absorbing material is dependent partially upon the individual that will be using the lenses.

Figure 3:
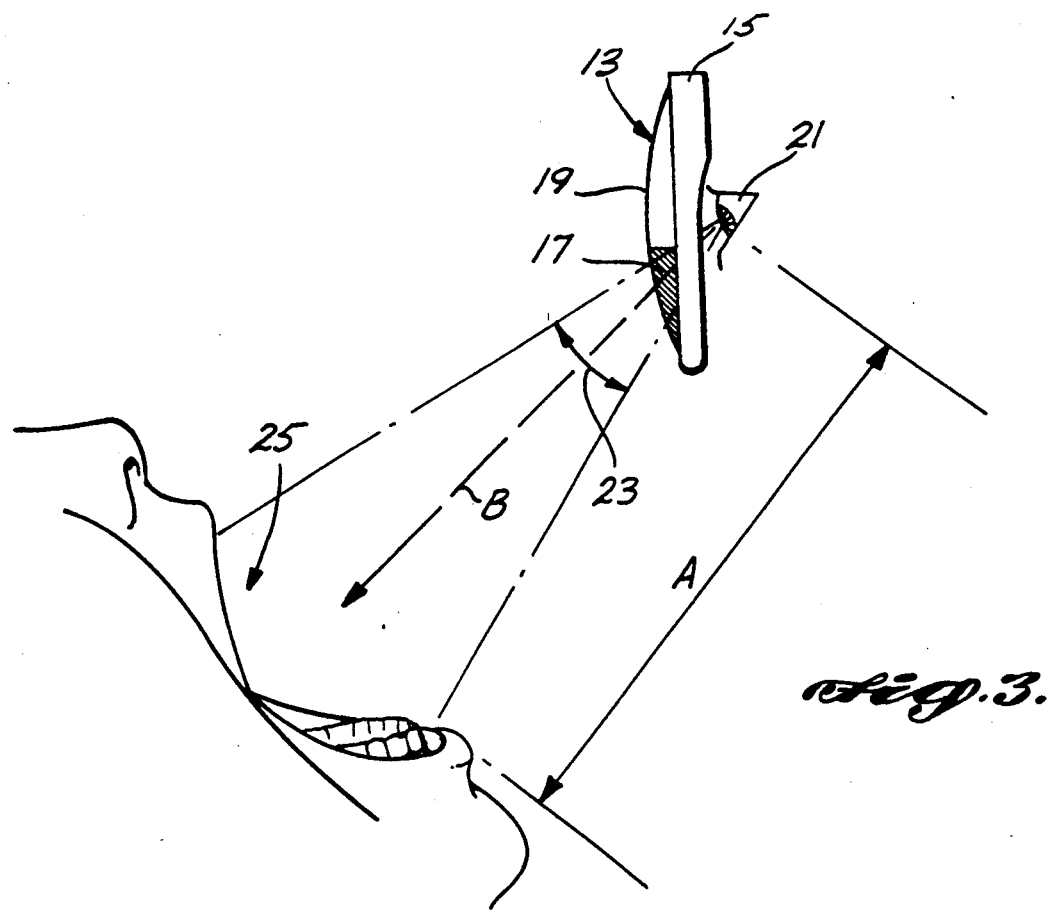
FIG. 3 is a schematic showing a lens formed in accordance with the present invention positioned between a wearer's eye and a patient's mouth, wherein the wearer is viewing through the coated portion of the lens.

Referring to FIG. 3, the portion of lenses 13 that are coated with the blue light absorbing material is such that at normal operating distances (identified by reference letter A) for dental workers, i.e., the general distance between the patient's mouth 25 and the dental worker's eye 21, the coated portion 17 subtends the angle 23 subtended at the wearer's eye 21 by the patient's mouth 25. In order to provide protection to the retina, the angle 23 should be considered as being subtended at the wearer's eye by the pupil. In this manner, the wearer's normal line of sight schematically shown as ray B, falls within the angle 23 such that the wearer is viewing the patient's mouth through the coated portion 17. By "patient's mouth," it is meant the portion between his upper lip and lower lip when the mouth is open and receiving the treatment that requires the intense light source. In this manner, the wearer is able to rely upon coated portion 17 of lenses 13 to shield his or her eyes from harmful blue light emitted by the light source, particularly light falling within the wearer's normal line of sight. Since the UV light absorbing coating is at least coextensive with the blue light absorbing coating, the eye is also shielded from harmful UV light emitted by the light source.

Figure 4:
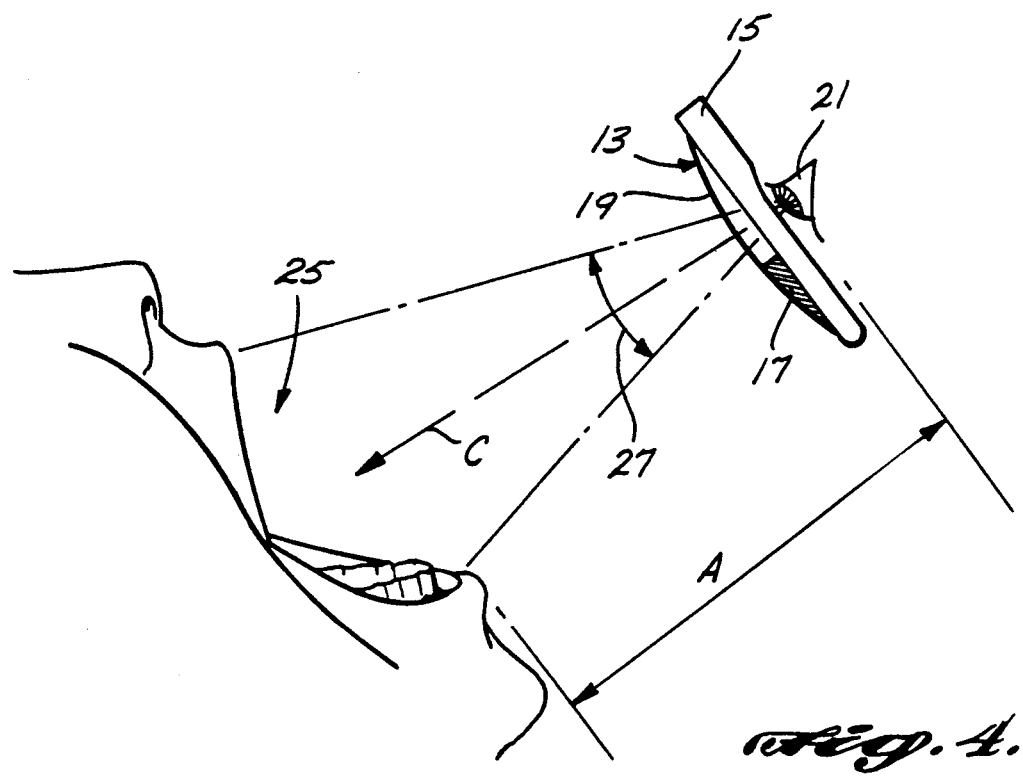
FIG. 4 is another schematic showing a lens formed in accordance with the present invention positioned such that the wearer is viewing the patient's mouth through the clear portion of the lens.

Referring to FIG. 4, when the light source is off and the wearer does not need protection from the ultraviolet light and blue light, the wearer can tilt his or her head down so that the clear portion 19 of lenses 13 subtends the angle 27 subtended at the wearer's eye 21 by the open mouth 25 of the patient. In this manner, the wearer's line of sight schematically shown as ray C, falls within angle 27 such that the wearer is viewing the patient's mouth through the clear portion 19. This allows the wearer to observe the treated area without a loss of contrast normally encountered when viewing the treated area through the coated portion 17.

It can be appreciated that the size of coated portion 17 depends on several factors, including the size of the angle subtended at the wearer's eye by the patient's mouth which is directly related to the distance between the patient's upper and lower lip when his or her mouth is open. The length of the normal working distance will also have an effect on the size of the angle subtended at the wearer's eye. Generally, the larger the opening of the patient's mouth, the larger the angle subtended at the wearer's eye and vice versa. Also, as the distance between the wearer's eye and the patient's mouth increases or decreases, the angle subtended decreases or increases respectively.

Although the present invention has been described in a specific form and as operating in a specific manner for the purposes of illustration, it is to be understood that the invention is not limited thereto. Various modifications will suggest themselves to those skilled in the art without departing from the spirit of this invention, the scope of which is set forth in the following claims.

The embodiments of the invention in which an exclusive property or privilege is claimed are defined as follows:

1. A lens for filtering visible and ultraviolet electromagnetic waves emitted by a source of electromagnetic waves used in a dental curing procedure, the lens comprising:

an ophthalmic lens, the ophthalmic lens including a first lens surface having a blocking portion that absorbs electromagnetic waves in the visible spectrum having a wavelength of about 530 nanometers or less and ultraviolet electromagnetic waves, and transmits electromagnetic waves in the visible spectrum having a wavelength of about 530 nanometers or greater, the blocking portion occupying less than a lower one-third of the first lens surface.

2. The lens of claim 1, wherein the electromagnetic waves in the visible spectrum having a wavelength of about 530 nanometers or less have wavelengths that fall in the blue region of the visible spectrum.

3. The lens of claim 1, wherein when the lens is positioned adjacent a wearer's eye such that the lens is between the wearer's eye and a patient's mouth, the blocking portion subtends an angle subtended at the wearer's eye by the patient's mouth when open.

4. The lens of claim 1, wherein the blocking portion occupies a sufficient amount of the lower half of the first lens surface to absorb electromagnetic waves in the visible spectrum having a wavelength of about 530 nanometers or less that are transmitted toward a wearer's eye within an angle subtended at the wearer's eye by an open mouth of a patient receiving the dental curing procedure when the lens is positioned adjacent the wearer's eye as an eyeglass lens at a normal working distance.

5. The lens of claim 1, wherein the lens is placed in an eyeglass frame worn on a wearer's head, a normal line of sight is defined through the lens such that a portion of the lens does not absorb electromagnetic waves in the visible spectrum subtends the angle substended at the wearer's eye by patient's mouth when open, the portion of the lens that absorbs electromagnetic waves in the visible spectrum having a wavelength of about 530 nanometers or less being dimensioned such that it can be placed in the normal line of sight to subtend the angle subtended at the wearer's eye by the patient's open mouth by shifting the wearer's head.

6. The lens of claim 1, wherein the ultraviolet electromagnetic waves are absorbed by a coating deposited onto the first lens surface.

7. The lens of claim 1, wherein the electromagnetic waves in the visible spectrum having a wavelength of about 530 nanometers or less are absorbed by a coating deposited on the first lens surface.

8. The lens of claim 6, further comprising a second lens surface opposite the first lens surface, wherein the ultraviolet electromagnetic waves are absorbed by a coating deposited on the second lens surface.

9. The lens of claim 7, further comprising a second lens surface, wherein the electromagnetic waves in the visible spectrum having a wavelength of about 530 nanometers or less are absorbed by a coating deposited on the second lens surface.

* * * * *

UNITED STATES PATENT AND TRADEMARK OFFICE
CERTIFICATE OF CORRECTION

PATENT NO. : 5,182,588
DATED : January 26, 1993
INVENTOR(S) : R. D. Maurer et al.

It is certified that error appears in the above-identified patent and that said Letters Patent is hereby corrected as shown below:

| COLUMN | LINE | |
|---|---|---|
| 2 | 15 | "a" should read --an-- |
| 2 | 42 | "opthalmic" should read --ophthalmic-- |
| 2 | 49 | "opthalmic" should read --ophthalmic-- |
| 2 | 52 | "opthalmic" should read --ophthalmic-- |
| 3 | 50 | "Prefearably" should read --Preferably-- |
| 6 | 42 | "substended" should read --subtended-- |//
(Claim 5, Line 5)

Signed and Sealed this

Seventh Day of December, 1993

Attest:

BRUCE LEHMAN

Attesting Officer

Commissioner of Patents and Trademarks